United States Patent [19]

Davies

[11] Patent Number: 4,877,793
[45] Date of Patent: Oct. 31, 1989

[54] THIENO[3,2-B]PYRIDINE-6-CARBOXA-MIDE COMPOUNDS USEFUL IN TREATING HYPERTENSION

[75] Inventor: Roy V. Davies, Nottingham, Great Britain

[73] Assignee: The Boots Company, PLC, Nottingham, England

[21] Appl. No.: 122,394

[22] Filed: Nov. 19, 1987

[30] Foreign Application Priority Data

Nov. 20, 1986 [GB] United Kingdom ............... 8627698

[51] Int. Cl.⁴ .......................................... C07D 213/32
[52] U.S. Cl. ..................................... 514/301; 546/114
[58] Field of Search ....................... 546/114; 514/301

[56] References Cited

U.S. PATENT DOCUMENTS

| | | | |
|---|---|---|---|
| 3,903,095 | 9/1975 | Shen et al. | 546/114 |
| 3,997,545 | 12/1976 | Kuwada et al. | 546/114 |
| 4,302,460 | 11/1981 | Davies et al. | 546/155 |
| 4,442,109 | 4/1984 | Davies | 546/153 |
| 4,447,435 | 5/1984 | Davies | 546/153 |
| 4,552,884 | 11/1985 | Sim et al. | 514/312 |
| 4,659,718 | 4/1987 | Davies et al. | 546/153 |
| 4,710,506 | 12/1987 | Davies et al. | 546/114 |

FOREIGN PATENT DOCUMENTS

| | | | |
|---|---|---|---|
| 0046990 | 3/1982 | European Pat. Off. | 546/114 |
| 126970 | 12/1984 | European Pat. Off. | 546/155 |
| 172004 | 2/1986 | European Pat. Off. | 546/153 |
| 206616 | 12/1986 | European Pat. Off. | 546/155 |

Primary Examiner—Mary C. Lee
Assistant Examiner—Zinna Northington-Davis
Attorney, Agent, or Firm—Donald A. Peterson; Herbert D. Hart, III

[57] ABSTRACT

Novel 7(4H)-thieno[3,2-b]pyridinones of the formula I,

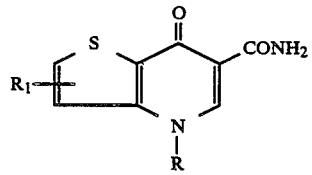

wherein R is lower alkyl, and $R_1$ is hydrogen, lower alkyl, lower alkoxy, halo, trifluoromethyl, or phenyl optionally substituted with one or two substituents selected from halo, lower alkyl, lower alkoxy and trifluoromethyl.

The compounds are useful in the treatment of cardiovascular diseases. Pharmaceutical compositions containing the novel compounds and processes for preparing the novel compounds are also described.

18 Claims, No Drawings

THIENO[3,2-B]PYRIDINE-6-CARBOXAMIDE COMPOUNDS USEFUL IN TREATING HYPERTENSION

This invention relates to novel thienopyridinones with therapeutic activity in the treatment of cardiovascular diseases, to therapeutic compositions containing the thienopyridinones and to processes for preparing the thienopyridinones.

The present invention provides novel 7(4$\underline{H}$)-thieno[3,2-b]pyridinones of the formula I,

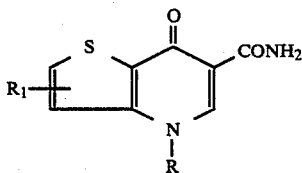

wherein R is lower alkyl, and $R_1$ is hydrogen, lower alkyl, lower alkoxy, halo, trifluoromethyl, or phenyl optionally substituted with one or two substituents selected from halo, lower alkyl, lower alkoxy and trifluoromethyl.

The term "lower" signifies a group with 1 to 4 carbon atoms. Any alkyl chain in the above-mentioned groups may be straight or branched. The term "halo" preferably signifies fluoro, chloro or bromo.

The substituent R is methyl, ethyl, n-, or isopropyl, or n-, sec-, iso- or tert-butyl. An especially preferred substituent is methyl.

In formula I, $R_1$ is hydrogen; lower alkyl, for example methyl or ethyl; lower alkoxy, for example methoxy or ethoxy; halo, for example chloro or fluoro; trifluoromethyl; or phenyl optionally substituted with one or two substituents selected from lower alkyl, for example methyl, lower alkoxy, for example methoxy, trifluoromethyl and halo, for example chloro. The optional substituents on the phenyl ring are preferably in the ortho- or meta-position, especially the ortho-position. Preferably $R_1$ is hydrogen, lower alkyl, lower alkoxy, halo or phenyl.

More particular compounds of formula I are those compounds in which R is methyl and $R_1$ is hydrogen, methyl, ethyl, methoxy, ethoxy, chloro, fluoro or phenyl. When $R_1$ is a substituent, it may be in the 2- or 3-position of the thienopyridinone nucleus, preferably in the 2-position.

In especially advantageous compounds of formula I, R is methyl and $R_1$ is hydrogen, 2-methyl, 2-chloro, 2-phenyl or 3-ethoxy, particularly hydrogen. The preferred compound of the invention is 4-methyl-7-oxo-4,7-dihydrothieno[3,2-b]pyridine-6-carboxamide.

The compounds of formula I may exist in anhydrous or hydrated form. For example, the compound 4-methyl-7-oxo-4,7-dihydrothieno[3,2-b]pyridine-6-carboxamide forms a monohydrate.

We have found that the compounds of formula I have valuable antihypertensive activity. The compounds reduce blood pressure when administered to hypertensive mammals.

The present invention provides pharmaceutical compositions which comprise a compound of formula I together with a pharmaceutically acceptable carrier.

As used hereinafter, the term "active compound" denotes a thienopyridinone of general formula I. In therapeutic use, the active compound may be administered orally, rectally, parenterally or topically, preferably orally. Thus the therapeutic compositions of the present invention may take the form of any of the known pharmaceutical compositions for oral, rectal, parenteral or topical administration. Pharmaceutically acceptable carriers suitable for use in such compositions are well known in the art of pharmacy. The compositions of the invention suitably contain 0.1-90% by weight of active compound. The compositions of the invention are generally prepared in unit dosage form.

Compositions for oral administration are the preferred compositions of the invention and these are the known pharmaceutical forms of such administration, for example tablets, capsules, syrups and aqueous or oily suspensions. The excipients used in the preparation of these compositions are the excipients known in the pharmacist's art. Tablets may be prepared by mixing the active compound with an inert diluent such as calcium phosphate in the presence of disintegrating agents, for example maize starch, and lubricating agents, for example magnesium stearate, and tableting the mixture by known methods. Such tablets may, if desired, be provided with enteric coatings by known methods, for example by the use of cellulose acetate phthalate. Similarly capsules, for example hard or soft gelatin capsules, containing the active compound with or without added excipients, may be prepared by conventional means and, if desired, provided with enteric coatings in a known manner. Enteric coated compositions of the invention may be advantageous, depending on the nature of the active compound. The tablets and capsules may conveniently each contain 1-500 mg of the active compound. Other compositions for oral administration include, for example, aqueous suspensions containing the active compound in an aqueous medium in the presence of a non-toxic suspending agent such as sodium carboxymethylcellulose, and oily suspensions containing a compound of the present invention in a suitable vegetable oil, for example arachis oil.

Compositions of the invention suitable for rectal administration are the known pharmaceutical forms for such administration, for example, suppositories with cocoa butter or polyethylene glycol bases.

Compositions of the invention suitable for parenteral administration are the known pharmaceutical forms for such administration, for example, sterile suspension in aqueous and oily media or sterile solutions in a suitable solvent.

Compositions for topical administration may comprise a matrix in which the active compound is dispersed so that the compound is held in contact with the skin in order to administer the active compound transdermally. Alternatively the active compound may be dispersed in a cream or ointment base.

In some formulations it may be beneficial to use the compounds of the present invention in the form of particles of very small size, for example, as obtained by fluid energy milling.

In the compositions of the present invention the active compound may, if desired, be associated with other compatible pharmacologically active ingredients, for example a $\beta$-blocker such as propranolol, oxprenolol, atenolol or timolol, or a diuretic such as bendrofluazide.

The therapeutic activity of the compounds of general formula I has been demonstrated by means of tests on standard laboratory animals. Such tests include, for example, the oral administration of the compounds to a strain of spontaneously hypertensive rat. Thus the compounds of formula I are useful for reducing blood pressure in hypertensive mammals. A suitable dose for enteral administration to mammals, including man, is generally within the range 0.1–25 mg/kg/day, more usually 0.5–10 mg/kg/day, given in single or divided doses. For parenteral administration, a suitable dose is generally within the range 0.01–5.0 mg/kg/day, especially 0.05–2.5 mg/kg/day. Oral administration is preferred.

Compounds of formula I have vasodilator activity with a dilating action on both arteriolar and venous vascular beds. Accordingly the compounds are indicated for use in the treatment of heart failure in mammals, including man. Suitable dosages are given above.

Compounds of formula I may be prepared by reacting ammonia with an acylating agent derived from an acid of formula II,

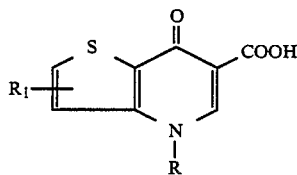

in which R and $R_1$ are as hereinbefore defined.

Suitable acylating agents include esters derived from compounds of formula II, for example lower alkyl esters such as the methyl ester or ethyl ester; acid anhydrides; mixed anhydrides with other acids such as ethoxyformic acid; and acyl halides, for example the acyl chloride. Depending upon the reaction conditions, the ammonia may be, for example, in the form of a gas which may be passed through a solution of an acylating agent, derived from an acid of formula II, in a suitable solvent, or the ammonia may be in the form of a solution in a suitable solvent, for example water or an alcohol such as ethanol. The reaction may be effected using methods analogous to those known in the art for preparing amides, e.g. carrying out the reaction in a sealed vesel under pressure.

Thus, for example, suitable acylating agents include esters of formula IIA,

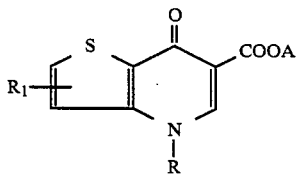

in which R and $R_1$ are as hereinbefore defined and A is lower alkyl.

Certain compounds of formula II and formula IIA in which R and $R_1$ are as hereinbefore defined are novel compounds.

The acylating agents derived from the acids of formula II may be prepared from the acids of formula II by methods known in the art, for example by reaction with thionyl chloride to give the corresponding acyl chloride.

The acids of formula II may be prepared by hydrolysis of lower alkyl esters of acids of formula II. The acids of formula II, the corresponding lower alkyl esters and other acylating agents derived therefrom may be prepared by methods known in the art. For example, the lower alkyl esters may be prepared by N-alkylation of a compound of the general formula III,

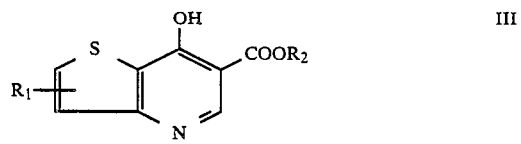

in which $R_1$ is as hereinbefore defined and $R_2$ is lower alkyl, preferably methyl or ethyl, for example by reaction with an alkyl halide, for example iodomethane, or a dialkyl sulphate, for example dimethyl sulphate.

Compounds of formula III may be prepared by the cyclisation of compounds of formula IV,

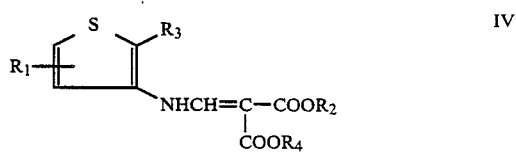

in which $R_1$ and $R^2$ are as hereinbefore defined, $R_3$ is hydrogen or carboxy and $R_4$ is lower alkyl. The cyclisation of compounds of formula IV may be carried out, for example, by heating the compounds at a temperature within the range 200° to 280°, for example by boiling a mixture of the compound and diphenyl ether under reflux.

Compounds of formula IV in which $R_3$ is carboxy may be prepared by reacting compounds of formula V,

in which $R_1$ is as hereinbefore defined and $R_3$ is carboxy, with compounds of formula VI,

in which $R_2$ and $R_4$ are as hereinbefore defined and $R_5$ is lower alkyl. For example compounds of formula V may be heated with compounds of formula VI, optionally in the presence of an inert solvent, e.g. toluene, to give compounds of formula IV. Compounds of formula IV in which $R_3$ is hydrogen may be prepared by reacting compounds of formula V in which $R_3$ is hydrogen or carboxy with compounds of formula VI. It will be appreciated by those skilled in the art that compounds of formula V in which $R_3$ is carboxy may be in the form of a salt, for example the sodium salt. In this case, the above-described reaction should be carried out in the presence of an acid, e.g. acetic acid.

Compounds of formula V in which $R_3$ is hydrogen may be prepared by methods known in the art. Compounds of formula V in which $R_3$ is carboxy may be prepared from compounds of formula VII,

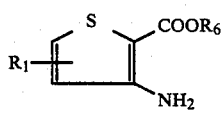 VII

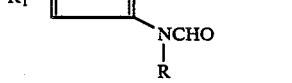 X in which $R_1$ is as hereinbefore defined and $R_6$ is lower alkyl, by known methods for converting carboxylic acid esters to carboxylic acids, for example by heating a compound of formula VII with aqueous sodium hydroxide, followed by treatment with an acid, for example hydrochloric acid. Compounds of formula VII may be prepared by methods known in the art.

Compounds of formula VI may be prepared by conventional methods.

Compounds of formula I may also be prepared by alkylation of compounds of formula VIII,

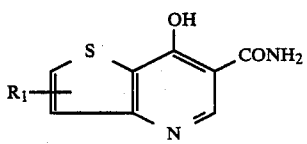 VIII in which $R_1$ is as hereinbefore defined. The alkylation may be carried out by reaction with, for example, an alkyl halide, for example iodomethane, or a dialkyl sulphate, for example dimethyl sulphate.

Compounds of formula VIII may be prepared by reacting ammonia with compounds of formula III or with acylating agents derived from compounds of formula III. The acylating agents may be derived from compounds of formula III by methods known in the art.

Compounds of formula I may also be prepared by removal of the group Q from compounds of formula IX,

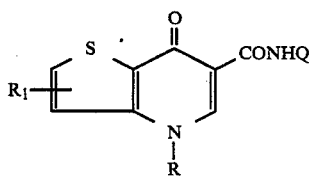 IX in which R and $R_1$ are as hereinbefore defined and Q is an amide-protecting group, for example, an optionally substituted diphenyl methyl group, a tert-butyl group or an optionally substituted benzyl group, e.g. methoxy substituted benzyl or benzyl, by conventional methods. For example, when Q is optionally substituted benzyl its removal may be effected by heating the compound with methanesulphonic acid.

Compounds of formula IX may be prepared from compounds of formula II, by analogous methods to those known in the art. For example, a compound of formula IX in which Q is benzyl may be prepared by the reaction of benzylamine with an acylating agent derived from a compound of formula II or by the reaction of a compound of formula II with a complex formed by reacting benzylamine with phosphorus trichloride.

Compounds of formula IX may also be prepared by the cyclisation of compounds of formula X, in which R, $R_1$ and Q are as hereinbefore defined, in the presence of a base, for example sodium methoxide.

Compounds of formula X may be prepared by the formylation of compounds of formula XI,

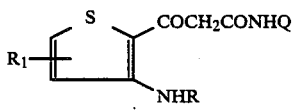 XI in which R, $R_1$ and Q are as hereinbefore defined, by using a formylating agent such as formic acetic anhydride.

Compounds of formula XI may be prepared by reacting compounds of formula XII,

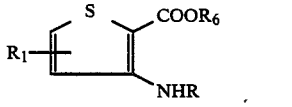 XII in which R, $R_1$ and $R_6$ are as hereinbefore defined with a compound of formula XIII, $$M^{\oplus \ominus}CH_2CON^{\ominus}QM^{\oplus} \qquad \text{XIII}$$

in which Q is as hereinbefore defined and M is an alkali metal, especially sodium or lithium.

Compounds of formula XII may be prepared from compounds of formula VII by methods known in the art, for example by reaction with an alkyl halide e.g. iodomethane.

Compounds of formula XIII may be prepared by reacting compounds of formula XIV with a suitable base, for example butyl lithium.

$$CH_3CONHQ \qquad \text{XIV}$$

Compounds of formula IX may also be prepared by reacting compounds of formula XI with a tri(lower alkyl)orthoformate, for example triethyl orthoformate, in an inert solvent, e.g. toluene, in the presence of an acid, e.g. acetic acid, or base, e.g. piperidine.

Compounds of formula I may also be prepared from compounds of formula XV,

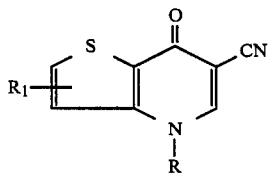 XV in which R and $R_1$ are as hereinbefore defined, by methods known in the art, for example by hydration of compounds of formula XV. The hydration may be effected, for example, by heating compounds of formula XV with a mineral acid, e.g. sulphuric acid, or a suitable base, e.g. aqueous sodium hydroxide.

Compounds of formula XV may be prepared by alkylation of compounds of formula XVI,

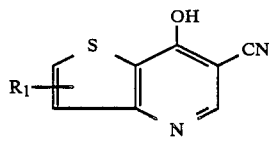    XVI in which $R_1$ is as hereinbefore defined, for example by reaction with an alkyl halide, e.g. iodomethane.

Compounds of formula XVI may be prepared by cyclisation of compounds of formula XVII,

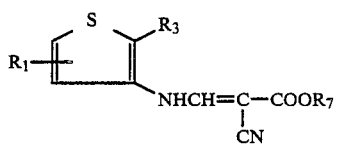    XVII in which $R_1$ and $R_3$ are as hereinbefore defined and $R_7$ is lower alkyl, for example by heating the compounds at a temperature within the range 200° to 280°, for example by boiling a mixture of the compound and diphenyl ether under reflux.

Compounds of formula XVI may be converted to compounds of formula VIII in a similar manner to that described for the conversion of compounds of formula XV to compounds of formula I.

Compounds of formula XVII may be prepared by reacting compounds of formula V, with compounds of formula XVIII,

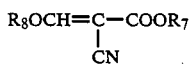    XVIII in which $R_7$ is as hereinbefore defined and $R_8$ is lower alkyl.

Compounds of formula XVIII may be prepared by conventional methods.

Compounds of formula XV may also be prepared by cyclising compounds of formula XIX,

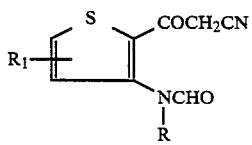    XIX in which R and $R_1$ are as hereinbefore defined, in the presence of a base, for example sodium methoxide.

Compounds of formula XIX may be prepared by reacting compounds of formula XX,

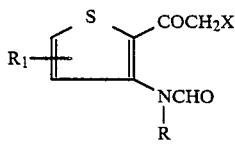    XX in which R and $R_1$ are as hereinbefore defined and X is halo, for example chloro or bromo, with a suitable cyanide, for example as provided by sodium cyanide.

Compounds of formula XX may be prepared by reacting compounds of formula XXI,

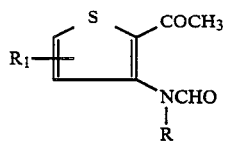    XXI in which R and $R_1$ are as hereinbefore defined, with a halogenating agent, for example, sulphuryl chloride, bromine or N-bromosuccinimide.

Compounds of formula XXI may be prepared by alkylating compounds of formula XXII,

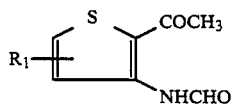    XXII in which $R_1$ is as hereinbefore defined, for example by reaction with an alkyl halide, for example iodomethane, in the presence of a suitable base, for example sodium hydride.

Compounds of formula XXII may be prepared by formylating compounds of formula XXIII,

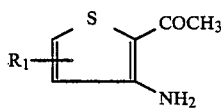    XXIII in which $R_1$ is as hereinbefore defined, for example by reaction with formic acetic anhydride.

Compounds of formula I in which $R_1$ is 2-lower alkoxy may be prepared by reacting the corresponding halo compound, in particular the bromo compound, with a suitable lower alkoxide, for example as provided by sodium methoxide, using methods that are known in the art for analogous reactions.

The invention is illustrated by the following non-limitative Examples, in which parts and percentages are by weight and compositions of mixed solvents are given by volume. Characterisation was by one or more of the following spectroscopic techniques: nuclear magnetic resonance, infra-red and mass spectroscopy. Temperatures are given in degrees Celsius.

As mentioned above, the therapeutic activity of the thienopyridinones of the present invention has been demonstrated by tests which include the oral administration of the compounds to a strain of spontaneously hypertensive rat. This test was carried out in the following way.

Female rats, weight range 180-240 g, of the Aoki-Okamoto strain of spontaneously hypertensive rat were used. The rats in groups of four were fasted overnight before administration of the test compound. Blood pressure was determined in the following way. The rats were placed in a cabinet kept at 38° C. with their tails protruding through holes in the cabinet. After 30 minutes in the cabinet blood pressure was measured using an inflatable cuff placed round the base of the tail and arterial pulsations monitored with a pneumatic pulse transducer. A pressure, greater than the expected blood pressure, was applied to the cuff, and this pressure was slowly reduced. The pressure in the cuff at which arterial pulsations reappeared was taken as the blood pressure. The rats were removed from the cabinet and each group orally dosed with a given dose of the test compound given as a solution or suspension in 0.25% aqueous carboxymethylcellulose. In addition to the pre-dose reading, blood pressure was measured at 1.5 and 5.0 hours after dosing. A compound was designated as active if at 90 mg/kg it gave a reduction of blood pressure equal to or greater than that considered to be the minimum significant reduction ($p<0.01$) on the basis of historical control data.

Compounds of formula I in which $R_1$ is as shown in Table 1 below gave the minimum significant reduction at the following dosages.

TABLE 1

| $R_1$ | Dose (mg/kg) |
| --- | --- |
| hydrogen | 30 |
| 2-phenyl | 3 |
| 2-methyl | 30 |
| 3-ethoxy | 30 |
| 2-chloro | 90 |

EXAMPLE 1

(a) Dimethyl sulphate (3.9 ml) was added to a stirred solution of ethyl 7-hydroxythieno[3,2-b]-pyridine-6-carboxylate (4.63 g) and potassium hydroxide (3.5 g) in water (50 ml) at 0°–5°. More water (20 ml) was added and the mixture was stirred at ambient temperature for 24 hours. The solid product was collected by filtration, washed with water and dried to give the novel compound ethyl 4-methyl-7-oxo-4,7-dihydrothieno[3,2-b]pyridine-6-carboxylate, m.p. 122°–128°.

(b) A mixture of the product from (a) (3.0 g) and aqueous ammonia (specific gravity 0.880, 60 ml) was stirred and heated on a steam bath. Effervescence occurred and octan-1-ol (2 ml) and more aqueous ammonia (specific gravity 0.880, 20 ml) were added and heating on the steam bath continued overnight. The mixture was then cooled to ambient temperature and the solid product collected by filtration, dried and crystallised from industrial methylated spirit to give the novel compound 4-methyl-7-oxo-4,7-dihydrothieno[3,2-b]pyridine-6-carboxamide, m.p. 255°–258°.

EXAMPLE 2

4-Methyl-7-oxo-4,7-dihydrothieno[3,2-b]pyridine-6-carboxamide was stored in a vessel at 25° at a relative humidity of 86% for five days. There was obtained 4-methyl-7-oxo-4,7-dihydrothieno[3,2-b]pyridine-6-carboxamide monohydrate, m.p. 252°–255°.

EXAMPLE 3

(a) A mixture of methyl 3-amino-5-phenylthiophene-2-carboxylate (9.6 g) and 0.9M aqueous sodium hydroxide solution (50 ml) was stirred and boiled under reflux for 4 hours to give a solution of sodium 3-amino-5-phenylthiophene-2-carboxylate.

(b) The solution from (a) was evaporated to dryness and the residue suspended in toluene (120 ml). A solution of glacial acetic acid (3.5 ml) in diethyl ethoxymethylenemalonate (8.9 g) was added to the toluene suspension and the mixture was boiled under reflux for 4 hours. The mixture was cooled and partitioned between dichloromethane (600 ml) and water (200 ml). The dichloromethane extract was dried over anhydrous magnesium sulphate and evaporated to give an oily solid which was triturated with cyclohexane to give a solid mixture of the novel compound diethyl[(5-phenyl-3-thienyl)amino]methylenemalonate and the novel compound 3-[2,2-bis(ethoxycarbonyl)vinylamino]-5-phenyl-2-thenoic acid.

(c) A solid mixture of products prepared as in (b) (85 g) was added with stirring during 25 minutes to refluxing diphenyl ether (800 ml) under nitrogen. The mixture was stirred and refluxed for a further 25 minutes then allowed to cool to room temperature, diluted with diethyl ether (2.5 l) and stirred at ambient temperature for 2 hours. The solid was collected, washed with diethyl ether and dried to give the novel compound ethyl 2-phenyl-7-hydroxythieno[3,2-b]pyridine-6-carboxylate, m.p. 286°–289°.

(d) A mixture of the product from (c) (39.0 g), potassium carbonate (22.0 g) and dry dimethylformamide (1100 ml) was stirred at ambient temperature for 30 minutes. Iodomethane (10 ml) was added to the mixture and stirring was continued for 24 hours. The dimethylformamide was removed by distillation under reduced pressure to give a residue which on trituration with water (1 l) gave the novel compound ethyl 4-methyl-7-oxo-2-phenyl-4,7-dihydrothieno[3,2-b]pyridine-6-carboxylate, m.p. 189°–191°.

(e) A mixture of the product from (d) (10 g) and 1M aqueous sodium hydroxide solution (100 ml) was stirred at 95°–100° for 2.5 hours. The mixture was filtered hot and the cooled filtrate acidified with 5M hydrochloric acid and then stirred overnight. The product was collected, washed with water and dried to give the novel compound 4-methyl-7-oxo-2-phenyl-4,7-dihydrothieno[3,2-b]pyridine-6-carboxylic acid, m.p. 290°–292°.

(f) The product (4 g) from (e) was finely ground and mixed with triethylamine (2 ml) and dry tetrahydrofuran (400 ml) and the mixture stirred at ambient temperature for 15 minutes. The suspension was cooled to 0° and a solution of ethyl chloroformate (1.5 ml) in dry tetrahydrofuran (25 ml) was added dropwise to the mixture during 10 minutes. Stirring was continued at 0°–5° for 1 hour and then a further quantity of ethyl chloroformate (0.2 ml) was added. The mixture was stirred for a further 15 minutes and then aqueous ammonia (specific gravity 0.880, 30 ml) was added. After 30 minutes, the stirred mixture was evaporated to dryness and the residue partitioned between water (100 ml) and dichloromethane (100 ml). The aqueous layer was further extracted with dichloromethane (2×100 ml) and the combined extracts were dried over anhydrous sodium sulphate and evaporated to give the novel compound 4-methyl-7-oxo-2-phenyl-4,7-dihydrothieno[3,2-b]pyridine-6-carboxamide, m.p. 266°–268°.

EXAMPLE 4

(a) A mixture of methyl 3-amino-5-methylthiophene-2-carboxylate (34 g) and 1.2M aqueous sodium hydroxide solution (500 ml) was stirred at 95°–100° for 3 hours, cooled to 4° and acidified with 5M hydrochloric acid. After standing for 30 minutes the product, 3-amino-5-methylthiophene-2-carboxylic acid, was collected, washed well with water and partially dried in vacuo at 20°.

(b) A mixture of the partially dried product from (a), diethyl ethoxymethylenemalonate (40 ml) and diethyl ether (10 ml) was stirred at 90°–95° for 2.5 hours in an apparatus set for distillation. When distillation of ethanol and diethyl ether ceased the residue was cooled to ambient temperature and dissolved in light petroleum ether (b.p. 40°-60°, 500 ml). The solution was dried over anhydrous magnesium sulphate and concentrated to 200 ml from which crystallised a mixture of the novel compounds diethyl[(5-methyl-3-thienyl)amino]methylenemalonate and 3-[2,2-bis(ethoxycarbonyl)-vinylamino]-5-methyl-2-thenoic acid.

(c) The mixture of products from (b) (10.0 g) was added with stirring during 10 minutes to refluxing diphenyl ether (300 ml) under nitrogen. The mixture was stirred and refluxed for a further 20 minutes then allowed to cool to room temperature. The mixture was diluted with diethyl ether (1 l) and left to stand for 1 hour at ambient temperature. The solid was collected, washed with more diethyl ether and dried to give the novel compound ethyl 2-methyl-7-hydroxythieno[3,2-b]pyridine-6-carboxylate, m.p. 240°-245°.

(d) A mixture of ethyl 2-methyl-7-hydroxythieno[3,2-b]pyridine-6-carboxylate (21 g), potassium carbonate (12.2 g) and dry dimethylformamide (750 ml) was stirred at ambient temperature and iodomethane (6 ml) added. The mixture was stirred at ambient temperature for approximately 3.5 hours, then at 60° for 2 hours. The solvent was removed under reduced pressure to give a residue which on treatment with water (300 ml) gave the novel compound ethyl 2,4-dimethyl-7-oxo-4,7-dihydrothieno[3,2-b]pyridine-6-carboxylate, m.p. 143°-144°.

(e) The product from (d) (3 g) was mixed with aqueous ammonia (specific gravity 0.880, 30 ml) and stirred at 95° for 8 hours. A further quantity of aqueous ammonia (20 ml) was added to the mixture and heating was continued for a further 8 hours. The solid was collected from the cooled mixture and dried to give crude 2,4-dimethyl-7-oxo-4,7-dihydrothieno[3,2-b]pyridine-6-carboxamide. The filtrate was acidified with 5M hydrochloric acid and allowed to stand for 20 minutes. A solid was collected and triturated with diethyl ether containing a little industrial methylated spirit, then dried to give the novel compound 2,4-dimethyl-7-oxo-4,7-dihydrothieno[3,2-b]pyridine-6-carboxylic acid, m.p. 305°-315°.

(f) A mixture of 2,4-dimethyl-7-oxo-4,7-dihydrothieno[3,2-b]pyridine-6-carboxylic acid (1.27 g), triethylamine (0.6 ml) and dry tetrahydrofuran (120 ml) was stirred at ambient temperature for 30 minutes. The mixture was cooled to 0° and a solution of ethyl chloroformate (0.6 ml) in dry tetrahydrofuran (10 ml) was added during 3 minutes, before being allowed to warm to ambient temperature. Stirring was continued for 18 hours and a further quantity of ethyl chloroformate (0.3 ml) was added at ambient temperature. After stirring for a further 2 hours, the mixture was cooled to 5° and aqueous ammonia (specific gravity 0.880, 10 ml) was added. The mixture was stirred for 20 minutes and the solid was collected, washed with water (50 ml) and dried to give a second sample of crude 2,4-dimethyl-7-oxo-4,7-dihydrothieno[3,2-b]pyridine-6-carboxamide. The two samples of the carboxamide from (e) and (f) were combined and crystallised from industrial methylated spirit to give pure novel compound 2,4-dimethyl-7-oxo-4,7-dihydrothieno[3,2-b]pyridine-6-carboxamide, m.p. 328°-330°.

EXAMPLE 5

(a) A mixture of 3-amino-4-ethoxythiophene (10 g) and diethyl ethoxymethylenemalonate (15.1 g) was stirred at 95° in an apparatus set for distillation. When ethanol evolution ceased (3 hours) the mixture was cooled to ambient temperature and the semi-solid was triturated with boiling petroleum ether (b.p. 60°-80°, 50 ml) then the mixture diluted with more petroleum ether (b.p. 60°-80, 300 ml). The solid was collected, washed with petroleum ether (b.p. 60°-80°) and dried to give the novel compound diethyl[(4-ethoxy-3-thienyl)amino]methylenemalonate, m.p. 108°-109°.

(b) A solution of the product from (a) (17.3 g) in diphenyl ether (60 ml) at 40° was added to stirred refluxing diphenyl ether (160 ml) during 20 minutes under nitrogen. Heating under reflux was continued for 20 minutes then the mixture cooling to ambient temperature. The mixture was diluted with diethyl ether (200 ml), the solid collected, washed with diethyl ether (100 ml) followed by industrial methylated spirit (50 ml) and then dried in vacuo at 100° to give the novel compound ethyl 3-ethoxy-7-hydroxythieno[3,2-b]pyridine-6-carboxylate, m.p. 223°-224°.

(c) A mixture of the product prepared as in (b) (31.5 g), anhydrous potassium carbonate (16.3 g) and dry dimethylformamide (500 ml) was stirred for 2 hours at ambient temperature. Iodomethane (10 ml) was added to the mixture during 10 minutes and stirring was continued for 24 hours at ambient temperature. In order to remove excess iodomethane aqueous ammonia (specific gravity 0.880, 10 ml) was added and the mixture was stirred for 1 hour and filtered. The filtrate was evaporated and the residue was stirred with water (700 ml) for 2 hours. A solid was collected, dried and crystallised from isopropyl alcohol to give the novel compound ethyl 3-ethoxy-4-methyl-7-oxo-4,7-dihydrothieno[3,2-b]pyridine-6-carboxylate, m.p. 198°-200°.

(d) Ethyl 3-ethoxy-4-methyl-7-oxo-4,7-dihydrothieno[3,2-b]pyridine-6-carboxylate (3 g) and a saturated solution of ammonia in ethanol (70 ml) were stirred together in a sealed stainless steel pressure vessel at 130° for 24 hours. After allowing to cool to ambient temperature the mixture was filtered and the solid was dried to give the novel compound 3-ethoxy-4-methyl-7-oxo-4,7-dihydrothieno[3,2-b]pyridine-6-carboxamide, m.p. 286°-287°.

EXAMPLE 6

(a) Potassium carbonate (0.56 g) was added to a stirred solution of ethyl 2-chloro-7-hydroxythieno[3,2-b]pyridine-6-carboxylate (1.1 g) in dry dimethylformamide (100 ml) at ambient temperature. After 5 minutes iodomethane (0.3 ml) was added to the mixture and stirring was continued for 18 hours. The mixture was stirred at 60° for 2 hours and then evaporated to dryness to give a residue which was dissolved in water (80 ml). The aqueous solution was extracted with dichloromethane (3×150 ml) and the combined extracts dried over anhydrous sodium sulphate and evaporated to give the novel compound ethyl 2-chloro-4-methyl-7-oxo-4,7-dihydrothieno[3,2-b]pyridine-6-carboxylate, m.p. 168°-171°.

(b) A mixture of ethyl 2-chloro-4-methyl-7-oxo-4,7-dihydrothieno[3,2-b]pyridine-6-carboxylate (1.6 g) and 0.35M aqueous sodium hydroxide solution (50 ml) was stirred at 95° for 3 hours. The mixture was cooled to 0° and acidified with 5M hydrochloric acid to pH 4. After 15 minutes the solid was collected, washed with water and stirred with a mixture of diethyl ether (60 ml) and industrial methylated spirit (10 ml) for 2 hours. The solid was collected and dried to give the novel compound 2-chloro-4-methyl-7-oxo-4,7-dihydrothieno[3,2-b]pyridine-6-carboxylic acid.

(c) The product from (b) (1.15 g) was mixed with a solution of triethylamine (0.7 ml) in dry tetrahydrofuran (100 ml) and stirred at ambient temperature for 20 minutes. The mixture was cooled to 0°-5° and a solution of ethyl chloroformate (0.5 ml) in dry tetrahydrofuran (10 ml) was added dropwise during 15 minutes. The resultant mixture was allowed to warm to 15° over 1 hour. A further quantity of ethyl chloroformate (0.2 ml) was added and the mixture was stirred at 15°-20° for 1 hour. The mixture was cooled to 5° and aqueous ammonia (specific gravity 0.880, 40 ml) was added. After 10 minutes the mixture was concentrated to half the original volume and allowed to stand for 18 hours. The solid was collected, washed with water and dried to give the novel compound 2-chloro-4-methyl-7-oxo-4,7-dihydrothieno[3,2-b]pyridine-6-carboxamide, m.p. 325°-327° (decomposes).

EXAMPLE 7

In the preparation of capsules, 100 parts by weight of active compound and 250 parts by weight of lactose are de-aggregated and blended. The mixture is filled into hard gelatin capsules, each capsule containing 100 mg of active compound.

EXAMPLE 8

Tablets are prepared from the following ingredients.

|  | parts by weight |
|---|---|
| Active compound prepared as in Example 1 | 100 |
| Lactose | 100 |
| Maize starch | 22 |
| Polyvinylpyrrolidone | 10 |
| Magnesium stearate | 3 |

The active compound, the lactose and some of the starch are de-aggregated, blended and the resulting mixture is granulated with a solution of the polyvinylpyrrolidone in ethanol. The dry granulate is blended with the magnesium stearate and the rest of the starch. The mixture is then compressed in a tableting machine to give tablets containing 100 mg active compound.

In the same way are prepared tablets containing active ingredients prepared as in Examples 2 to 6.

EXAMPLE 9

Tablets are prepared by the method of Example 8. The tablets are enteric coated in a conventional manner using a solution of 20% cellulose acetate phthalate and 3% diethyl phthalate in ethanol:dichloromethane 1:1.

EXAMPLE 10

In the preparation of suppositories, 100 parts by weight of active compound is incorporated in 1300 parts by weight of tri-glyceride suppository base and the mixture formed into suppositories each containing 100 mg of active compound.

I claim:
1. A compound of the formula,

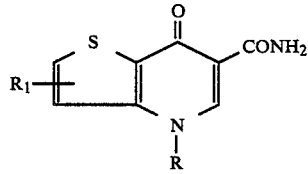

in which R is lower alkyl, and $R_1$ is hydrogen, lower alkyl, lower alkoxy, halo, trifluoromethyl, or phenyl unsubstituted or substituted with one or two substituents selected, from the group consisting of halo, lower alkyl, lower alkoxy and trifluoromethyl.

2. A compound according to claim 1 in which $R_1$ is hydrogen, lower alkyl, lower alkoxy, halo or phenyl.

3. A compound according to claim 1 in which R is methyl and $R_1$ is hydrogen, methyl, ethyl, methoxy, ethoxy, chloro, fluoro or phenyl.

4. A compound according to claim 1 in which R is methyl and $R_1$ is hydrogen, 2-methyl, 2-chloro, 2-phenyl or 3-ethoxy.

5. The compound according to claim 1 which is 4-methyl-7-oxo-4,7-dihydrothieno[3,2-b]pyridine-6-carboxamide.

6. The compound according to claim 1 which is 4-methyl-7-oxo-4,7-dihydrothieno[3,2-b]pyridine-6-carboxamide monohydrate.

7. A pharmaceutical composition in unit dosage form useful for treating hypertension in humans which comprises an antihypertensively effective amount of a compound of the formula

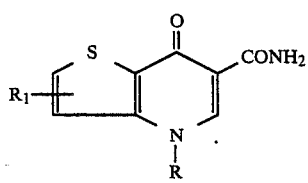

in which R is lower alkyl, and $R_1$ is hydrogen, lower alkyl, lower alkoxy, halo, trifluoromethyl, or phenyl unsubstituted or substituted with one or two substituents selected from the group consisting of halo, lower alkyl, lower alkoxy and trifluoromethyl, in combination with a pharmaceutically acceptable carrier.

8. A composition according to claim 7 wherein the compound is 4-methyl-7-oxo-4,7-dihydrothieno[3,2-b]pyridine-6-carboxamide.

9. A method of treating hypertension in humans which comprises administering to a human in need thereof a therapeutically effective amount of a compound of the formula

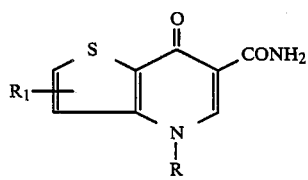

in which R is lower alkyl, and $R_1$ is hydrogen, lower alkyl, lower alkoxy, halo, trifluoromethyl, or phenyl unsubstituted or substituted with one or two substituents selected from the group consisting of halo, lower alkyl, lower alkoxy and trifluoromethyl, in combination with a pharmaceutically acceptable carrier.

10. A method according to claim 9 wherein the compound is 4-methyl-7-oxo-4,7-dihydrothieno[3,2-b]pyridine-6-carboxamide.

11. A composition according to claim 7 wherein $R_1$ is hydrogen, lower alkyl, lower alkoxy, halo, or phenyl.

12. A composition according to claim 7 wherein R is methyl and $R_1$ is hydrogen, methyl, ethyl, methoxy, ethoxy, chloro, fluoro, or phenyl.

13. A composition according to claim 7 wherein R is methyl and $R_1$ is hydrogen, 2-methyl, 2-chloro, 2-phenyl or 3-ethoxy.

14. A composition according to claim 7 wherein the compound is 4-methyl-7-oxo-4,7-dihydrothieno[3,2-b]pyridine-6-carboxamide monohydrate.

15. A method according to claim 9 wherein $R_1$ is hydrogen, lower alkyl, lower alkoxy, halo, or phenyl.

16. A method according to claim 9 wherein R is methyl and $R_1$ is hydrogen, methyl, ethyl, methoxy, ethoxy, chloro, fluoro, or phenyl.

17. A method according to claim 9 wherein R is methyl and $R_1$ is hydrogen, 2-methyl, 2-chloro, 2-phenyl or 3-ethoxy.

18. A method according to claim 9 wherein the compound is 4-methyl-7-oxo-4,7-dihydrothieno[3,2-b]pyridine-6-carboxamide monohydrate.

* * * * *